US009322040B2

(12) United States Patent
Zhang et al.

(10) Patent No.: US 9,322,040 B2
(45) Date of Patent: Apr. 26, 2016

(54) *PSEUDONOCARDIA* SP. AND METHOD FOR PREPARING DEOXYNYBOQUINONE BY UTILIZING SAME

(75) Inventors: Si Zhang, Guangzhou (CN); Changsheng Zhang, Guangzhou (CN); Xinpeng Tian, Guangzhou (CN); Sumei Li, Guangzhou (CN); Wenjun Zhang, Guangzhou (CN); Haibo Zhang, Guangzhou (CN); Guangtao Zhang, Guangzhou (CN); Hao Yin, Guangzhou (CN); Jianhua Ju, Guangzhou (CN)

(73) Assignee: SOUTH CHINA SEA INSTITUTE OF OCEANOLOGY, CHINESE ACADEMY OF SCIENCES, Guangzhou (CN)

( * ) Notice: Subject to any disclaimer, the term of this patent is extended or adjusted under 35 U.S.C. 154(b) by 190 days.

(21) Appl. No.: 13/885,568

(22) PCT Filed: Sep. 1, 2011

(86) PCT No.: PCT/CN2011/079232
§ 371 (c)(1),
(2), (4) Date: May 15, 2013

(87) PCT Pub. No.: WO2013/023391
PCT Pub. Date: Feb. 21, 2013

(65) Prior Publication Data
US 2013/0230890 A1 Sep. 5, 2013

(30) Foreign Application Priority Data
Aug. 12, 2011 (CN) .......................... 2011 1 0231994

(51) Int. Cl.
*C12P 17/18* (2006.01)
*C12N 1/20* (2006.01)
*C12R 1/01* (2006.01)

(52) U.S. Cl.
CPC ................. *C12P 17/182* (2013.01); *C12N 1/20* (2013.01); *C12R 1/01* (2013.01)

(58) Field of Classification Search
None
See application file for complete search history.

(56) References Cited

U.S. PATENT DOCUMENTS 6,645,752 B2 * 11/2003 Kamachi et al. ........... 435/252.1

OTHER PUBLICATIONS

Xin-Peng Tian; Li-Juan Long; Su-Mei Li; Jing Zhang; Ying Xu; Jie He; Jie Li; Fa-Zuo Wang; Wen-Jun Li; Chang-Sheng Zhang; and Si Zhang "Pseudonocardia antitumoralis sp. nov., a deoxynyboquinone-producing actinomycete isolated from a deep-sea sediment"IJSEM, (Mar. 2013) Pub. online May 25, 2012, 63(3), pp. 893-899. (doi: 10.1099/ijs.0.037135-0).*

Xin-Peng Tian; Li-Juan Long; Su-Mei Li; Jing Zhang; Ying Xu; Jie He; Jie Li; Fa-Zuo Wang; Wen-Jun Li; Chang-Sheng Zhang; and Si Zhang "Pseudonocardia antitumoralis sp. nov., a deoxynyboquinone-producing actinomycete isolated from a deep-sea sediment"IJSEM, (May 2013), 63(3), pp. 1936. (doi: 10.1099/ijs.0.X00005-0 ).*

Olano, Carlos et al.: "Antitumor Compounds from Marine Actinomycetes," Marine Drugs, (2009) 7, pp. 210-248 ISSN 1660-3397.

Bair, Joseph S., et al.: "Chemistry and Biology of Deoxynyboquinone, a Potent Inducer of Cancer Cell Death," J. Am. Chem. Soc., (2010) 12, pp. 5469-5478.

Tian, Xin-Peng, et al.: "Sciscionella marina gen. nov., sp. nov., a marine actinomycete isolated from a sediment in the northern South China Sea," International Journal of Systematic and Evolutionary Microbiology, (2009), 59, pp. 222-228.

Stackebrandt, Erko, et al.: "Taxonomic parameters revisited: tarnished gold standards," Microbiology Today, (2006) pp. 152-155.

Bhatnagar, Ira, et al.: "Marine Antitumor Drugs: Status, Shortfalls and Strategies," Marine Drugs, (2010) 8, pp. 2702-2720, ISSN 1660-3397.

Li, Sumei, et al.: "Pseudonocardians A-C, New Diazaanthraquinone Derivatives from a Deap-Sea Actinomycete Pseudonocardia sp. SCSIO 01299," Marine Drugs (2011) 9, pp. 1428-1439, ISSN 1660-3397.

International Search Report for PCT/CN2011/0679232 dated May 24, 2012 , 3 pages.

* cited by examiner

*Primary Examiner* — Thane Underdahl
*Assistant Examiner* — Aaron J Kosar
(74) *Attorney, Agent, or Firm* — Westerman, Hattori, Daniels & Adrian, LLP

(57) ABSTRACT

The invention discloses a *Pseudonocardia* sp. and a method for preparing Deoxynyboquinone by utilizing the same. *Pseudonocardia* sp. SCSIO 01299 was collected in China Center for Type Culture Collection (CCTCC) (Address: Wuhan University, Wuhan City, China) with the collection number of CCTCC NO: M 2011255 on Jul. 18, 2011. The *Pseudonocardia* sp. SCSIO 01299 can produce antibiotic Deoxynyboquinone, so that the *Pseudonocardia* sp. SCSIO 01299 can be utilized for preparing Deoxynyboquinone and a new way is provided for producing antibiotic Deoxynyboquinone with anti-tumor activity.

3 Claims, 4 Drawing Sheets

PSEUDONOCARDIA SP. AND METHOD FOR PREPARING DEOXYNYBOQUINONE BY UTILIZING SAME

FIELD OF THE INVENTION

The invention belongs to the field of industrial microbiology and specifically relates to a *Pseudonocardia* sp. SCSIO 01299 new species capable of producing antibiotic Deoxynyboquinone, as well as a method for preparing antibiotic Deoxynyboquinone by utilizing the same.

BACKGROUND OF THE INVENTION

Deoxynyboquinone (DNQ) is a compound which has been artificially synthesized, the structure is as shown in Formula (I), and the compound has significant cytotoxin activity and shows excellent characteristics, namely the stronger activity can be still shown under anoxic conditions and the medicine-making potential is great in anti-tumor medicaments taking the production of reactive oxygen species (ROS) as a resistance mechanism. The activity of a compound SCH 538415 with the similar structure is 10 times weaker than the activity of Deoxynyboquinone [Bair, J. S.; Palchaudhuri, R.; Hergenrother, P. J., Chemistry and biology of deoxynyboquinone, a potent inducer of cancer cell death. *J Am Chem Soc* 2010, 132, (15), 5469-78.].

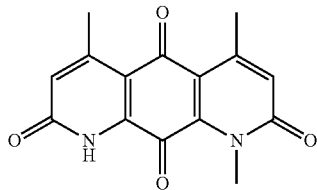

Formula (I)

SUMMARY OF THE INVENTION

The first object of the invention is to provide a *Pseudonocardia sp. SCSIO* 01299, which was collected in China Center for Type Culture Collection (CCTCC) (Address: Wuhan University, Wuhan City, China) with the collection number of CCTCC NO: M 2011255 on Jul. 18, 2011.

The *Pseudonocardia* sp. SCSIO 01299 disclosed by the invention is obtained by separation from submarine sediment 3258 m underwater in the northern South China Sea (E 120°0.975', N 19°0.664'). The conventional PCR (polymerase chain reaction) amplification is performed on 16S rDNA of the *Pseudonocardia* sp. SCSIO 01299, sequencing is performed, the sequence is as shown in SEQ ID NO.1, and then is submitted to GenBank, and the sequence number JN204514 is further obtained. The BLAST analysis is performed on the nucleotide sequence of the 16S rDNA, and the result shows that the similarity between the strain and *Pseudonocardia autotrophica* IMSNU 20050$^T$ is 98%, indicating that the strain SCSIO 01299 is *Pseudonocardia*.

As shown in FIG. 1, the phylogenetic relationship between the strain and one group of *Pseudonocardia* species is clearly disclosed through a neighbor-joining method, showing that the strain belongs to one of the *Pseudonocardia*.

Morphological characteristics and physiological and biochemical analyses are as follows:

The strain belongs to Gram-positive and aerobic actinomycete, basal filaments are yellowish and branched, and aerial mycelia are white, branched and differentiated into curled spore chains; and spores are shaped like rods (FIG. 2), 1.3-2.5 μm long and smooth in surfaces. Czapek's agar can produce soluble pigments. The strain can hydrolyze starch, cellulose and Tweens 20, 40 and 60, is negative in gelatin liquefaction, milk solidification and peptonization, can produce $H_2S$ and hydrolyze Tween 80 and is negative in oxidase and nitrate reduction reaction. The strain is positive in catalase reaction, can produce melanin and is negative in urease reaction. The strain can utilize D-arabinose, D-cellobiose, oxalate, D-galactose, D-glucose, inositol, D-maltose, D-mannitol, D-mannose, D-raffinose, L-rhamnose, D-ribose, D-sucrose, galactitol, D-lactose, D-sorbose, xylitol, fructose or D-xylose as a sole carbon source and energy source for growth, and can not utilize D-trehalose for growth. The tolerance ranges of pH, salt concentration and temperature are 6.0-8.0, 0-15% and 4-40° C. respectively. Meso-DAP is contained in cell walls. Phospholipid components are PG, DPG, PE, PI, PIM and unknown phospholipid PL. The dominant quinone is MK-8(H4). The main fatty acids are i-C16:0, i-C16:1 H, ai-C17:0 and i-C17:1 w9c. The molar content of G+C is 73.2(±0.5)%. According to the above morphological, physiological, chemical and other types of analyses, the strain is greatly different from the known proximate strain *Pseudonocardia autotrophica* IMSNU 20050$^T$, genomic hybridization further shows that the hybridization value between the strain and the most similar strain is 36%, which is far lower than 70% being the intraspecies variation standard [Stackebrandt, E. & Ebers, J. Taxonomic parameters revisited: tarnished gold standards. *Microbiol Today*. (2006). 33, 152-155.]. Therefore, by comprehensively analyzing multiple items of classified data, the strain is identified as a new species of *Pseudonocardia*, and is named as the *Pseudonocardia* sp. SCSIO 01299, and the strain was collected in China Center for Type Culture Collection (CCTCC) (Address: Wuhan University, Wuhan City, China) with the collection number of CCTCC NO: M 2011255 on Jul. 18, 2011.

In the invention, it is founded that the *Pseudonocardia* sp. SCSIO 01299 can produce antibiotic Deoxynyboquinone. Therefore, the second object of the invention is to provide a method for preparing antibiotic Deoxynyboquinone, and Deoxynyboquinone is obtained by preparation and separation from a fermentation culture of the *Pseudonocardia sp.* SCSIO 01299.

Preferably, antibiotic Deoxynyboquinone is obtained by preparation and separation from the fermentation culture of the *Pseudonocardia* sp. SCSIO 01299 through the following method, and the specific steps are as follows:

a) preparing the fermentation culture of the *Pseudonocardia sp.* SCSIO 01299, separating fermentation liquid of the fermentation culture from mycelia, extracting the fermentation liquid with butanone, and performing distillation and concentration on a butanone layer to get an extract A; and firstly leaching the mycelia with acetone, recovering acetone from a leaching solution, then extracting the remaining water mixed solution with butanone, and performing distillation and concentration on the butanone layer to get an extract B;

b) performing silica gel column chromatography on the extract A or the extract B or a crude extract obtained by mixing the extract A and the extract B, performing gradient elution using chloroform/methanol as eluent in the volume ratio of 100:0 to 0:100, and collecting a fraction Fr.1 which is obtained by gradient elution when the chloroform/methanol volume ratio is 100:1, further passing through an LH-20 gel column, eluting by taking the chloroform/methanol in the volume ratio of 1:1 as a mobile phase, and further performing recrystallization to get Deoxynyboquinone. Preferably, the fermentation culture of the *Pseudonocardia* sp. SCSIO 01299 prepared in the step a) is prepared through the following method: inoculating the activated *Pseudonocardia* sp. SCSIO 01299 into a seed culture medium, culturing at 28° C. and 200 rpm for 48 h to prepare seed liquid, inoculating the seed liquid into a fermentation culture medium according to 10% inoculation amount, and performing shaking culture at 28° C. and 200 rpm for 120 h to prepare the fermentation culture, wherein the formulae of the seed culture medium and the fermentation culture medium are as follows: each liter of each culture medium contains 15 g of starch, 5 g of soybean meal, 15 g of peptone, 15 g of glycerin, 2 g of $CaCO_3$, 30 g of crude sea salt and the balance of water, and the pH is 7.4. The content of Deoxynyboquinone in the fermentation culture of the *Pseudonocardia* sp. SCSIO 01299 prepared by the method is higher.

As the *Pseudonocardia* sp. SCSIO 01299 disclosed by the invention can produce antibiotic Deoxynyboquinone, the third object of the invention is to provide an application of the *Pseudonocardia* sp. SCSIO 01299 in the preparation of Deoxynyboquinone.

The *Pseudonocardia* sp. SCSIO 01299 disclosed by the invention is a new species of *Pseudonocardia*, and the strain can produce antibiotic Deoxynyboquinone with anti-tumor activity, thereby providing a new method for preparing Deoxynyboquinone.

The *Pseudonocardia* sp. SCSIO 01299 disclosed by the invention was collected in China Center for Type Culture Collection (CCTCC) (Address: Wuhan University, Wuhan City, China) with the collection number of CCTCC NO: M 2011255 on Jul. 18, 2011.

DETAILED DESCRIPTION OF THE EMBODIMENTS

The following embodiments are used for further describing the invention rather than limiting the invention.

Embodiment 1

I. Separation and Identification of *Pseudonocardia* sp. SCSIO 01299

As for extraction of genome DNA (deoxyribonucleic acid), PCR amplification of 16S rDNA, sequence alignment and an establishment method of a phylogenetic tree, as well as physiological, chemical and morphological identification and the like, involved in the identification of *Pseudonocardia* sp. SCSIO 01299, please see references [Tian, X. P., Zhi, X. Y., Qiu, Y. Q., Zhang, Y. Q., Tang, S. K., Xu, L. H., Zhang, S., Li, W. J. *Sciscionella marina* gen. nov., sp. nov., a marine actinomycete isolated from a sediment in the northern South China Sea. *Int J Syst Evol Microbiol,* 2009, 59(Pt 2): 222-228].

The *Pseudonocardia* sp. SCSIO 01299 disclosed by the invention is obtained by separation from submarine sediment 3258 m underwater in the northern South China Sea (E 120°0.975', N 19°0.664'). A separation culture medium is an ISP5 (International Streptomyces Project 5) culture medium in the prior art, each liter of the culture medium contains 1.0 g of L-asparaginic acid, 10.0 g of glycerin, 1.0 g of $K_2HPO_4$, 1 ml of trace element solution, 20.0 g of agar and 1000 ml of distilled water, and the pH is 7.2, wherein the *trace element solution contains 0.1 g of $FeSO_4.7H_2O$, 0.1 g of $MnCl_2.4H_2O$ and 0.1 g of $ZnSO_4.7H_2O$. The separation culture conditions are and 14 days. A strain SCSIO 01299 (*Pseudonocardia* sp. SCSIO 01299) is obtained by separation and purification from the submarine sediment.

Figure 1:
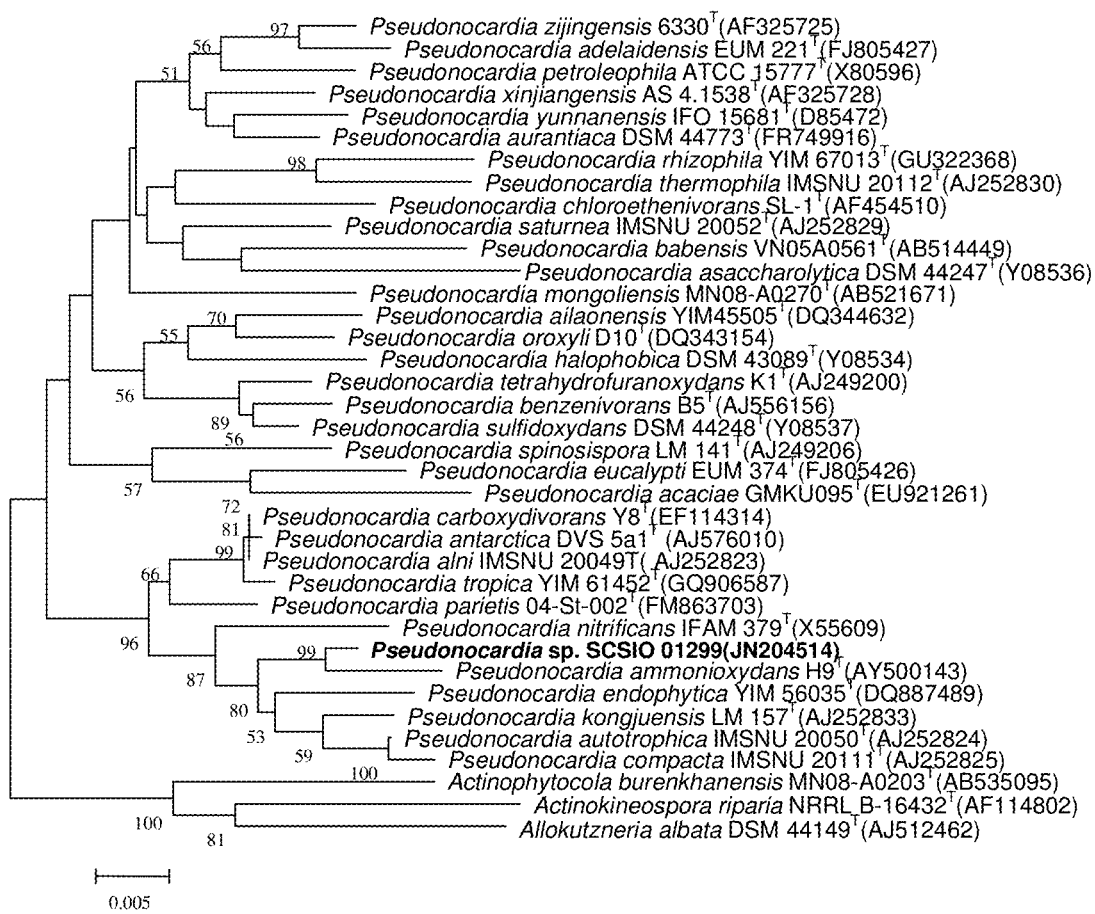
FIG. 1 is a phylogenetic tree of relationship among *Pseudonocardia* sp. SCSIO 01299 and species having the closest kinship therewith, which is reconstructed based on a neighbor-joining method of a 16s rDNA sequence.

The genome DNA of the strain SCSIO 01299 is extracted according to the method in the references or the conventional method, conventional PCR amplification is performed on 16S rDNA of the strain, sequencing is performed, the sequence is as shown in SEQ ID NO.1, and then is submitted to GenBank, and the sequence number JN204514 is further obtained. The BLAST analysis is performed on the nucleotide sequence of the 16S rDNA, and the result shows that the similarity between the strain and *Pseudonocardia autotrophica* IMSNU $20050^T$ is 98%, indicating that the strain SCSIO 01299 is *Pseudonocardia*. As shown in FIG. 1, the phylogenetic relationship between the strain and one group of *Pseudonocardia* species is clearly disclosed through a neighbor-joining method, showing that the strain belongs to one of the *Pseudonocardia*.

Figure 2:
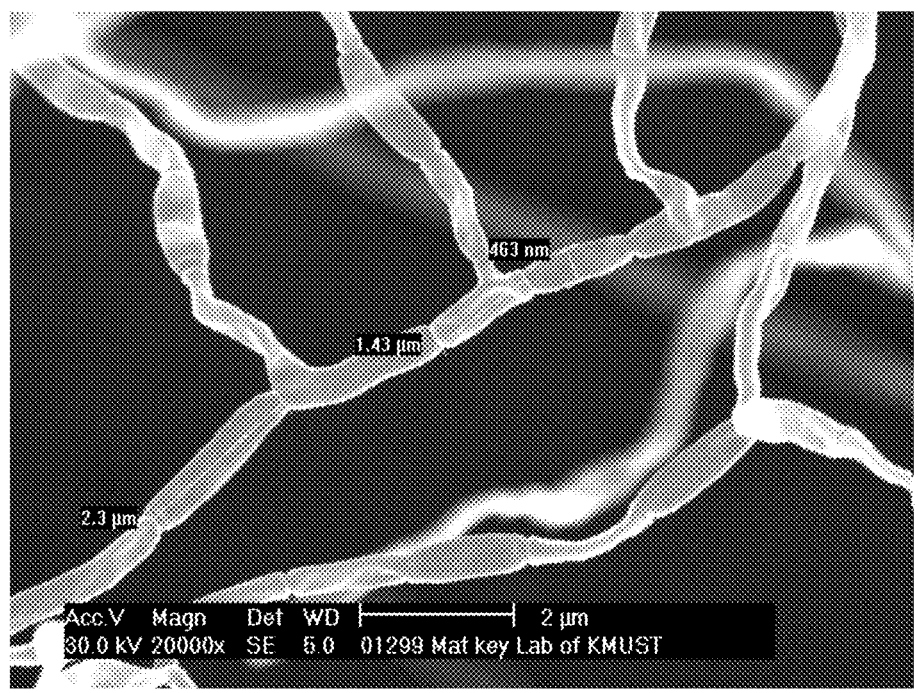
FIG. 2 is a scanning electron micrograph of spore morphology of *Pseudonocardia* sp. SCSIO 01299.

Morphological characteristics and physiological and biochemical analyses are as follows:

The strain SCSIO 01299 belongs to Gram-positive and aerobic actinomycete, basal filaments are yellowish and branched, and aerial mycelia are white, branched and differentiated into curled spore chains; and spores are shaped like rods (FIG. 2), 1.3-2.5 μm long and smooth in surfaces. Czapek's agar can produce soluble pigments. The strain can hydrolyze starch, cellulose and Tweens 20, 40 and 60, is negative in gelatin liquefaction, milk solidification and peptonization, can produce $H_2S$ and hydrolyze Tween 80 and is negative in oxidase and nitrate reduction reaction. The strain is positive in catalase reaction, can produce melanin and is negative in urease reaction. The strain can utilize D-arabinose, D-cellobiose, oxalate, D-galactose, D-glucose, inositol, D-maltose, D-mannitol, D-mannose, D-raffinose, L-rhamnose, D-ribose, D-sucrose, galactitol, D-lactose, D-sorbose, xylitol, fructose or D-xylose as a sole carbon source and energy source for growth, and can not utilize D-trehalose for growth. The tolerance ranges of pH, salt concentration and temperature are 6.0-8.0, 0-15% and 4° C. respectively. Meso-DAP is contained in cell walls. Phospholipid components are PG, DPG, PE, PI, PIM and unknown phospholipid PL. The dominant quinone is MK-8(H4). The main fatty acids are i-C16:0, i-C16:1 H, ai-C17:0 and i-C17:1 w9c. The molar content of G+C is 73.2(±0.5)%. According to the above morphological, physiological, chemical and other types of analyses, the strain is greatly different from the known proximate strain *Pseudonocardia autotrophica* IMSNU 20050$^T$, genomic hybridization further shows that the hybridization value between the strain and the most similar strain is 36%, which is far lower than 70% being the intraspecies variation standard (Stackebrandt, E. & Ebers, J. Taxonomic parameters revisited: tarnished gold standards. *Microbiol Today*. (2006). 33, 152-155). Therefore, by comprehensively analyzing multiple items of classified data, the strain is identified as a new species of *Pseudonocardia*, and is named as the *Pseudonocardia* sp. SCSIO 01299, and the strain was collected in China Center for Type Culture Collection (CCTCC) (address: Wuhan University, Wuhan City, China) with the collection number of CCTCC NO: M 2011255 on Jul. 18, 2011.

II. Separation and Preparation of Deoxynyboquinone

1. Culture Medium

A. Seed culture medium: each liter of the culture medium contains 15 g of starch, 5 g of soybean meal, 15 g of peptone, 15 g of glycerin, 2 g of $CaCO_3$, 30 g of crude sea salt and the balance of water, and the pH is 7.4. Sterilization is performed at 121° C. for 30 min;

B. Fermentation culture medium: the formula the same as that of the seed culture medium is utilized. Sterilization is performed at 121° C. for 30 min.

2. Fermentation 2.1 Seed culture: respectively inoculating single colonies of the activated *Pseudonocardia* sp. SCSIO 01299 on a culture dish into 18 flasks, wherein each flask is a 250 mL conical culture flask containing 50 mL of the seed culture medium; and culturing at 28° C. and 200 r·min$^{-1}$ for 48 h to prepare 900 mL of seed liquid. 2.2 Fermentation culture: inoculating the seed liquid into 9 L of the fermentation culture medium (placed in 250 mL conical culture flasks, wherein each flask contains 50 ml of the fermentation culture medium, and the total number of the flasks is 180) according to 10% inoculation amount, performing shaking culture at 28° C. and 200 r·min$^{-1}$ for 120 h to prepare 9 L of fermentation culture.

3. Extraction

Centrifugal separation (3500 r·min$^{-1}$, 8 min) is firstly performed on the fermentation culture to get 9 L in volume of the supernatant fluid (fermentation liquid) and the mycelia. The fermentation liquid is extracted by 18 L of butanone four times, extraction liquid is mixed, and distillation and concentration are performed on a butanone layer to get the extract of the supernatant fluid (extract A) (11.3 g); and the mycelia is leached by 2 L of acetone three times and 3 hours each time, acetone is recovered from extraction solution in a decompression manner, the remaining water mixed solution is extracted by 6 L of butanone, and decompression and distillation are performed on the butanone layer to get the extract of the mycelia (extract B) (3.2 g).

4. Extraction and separation of compound Deoxynyboquinone

Figure 3:
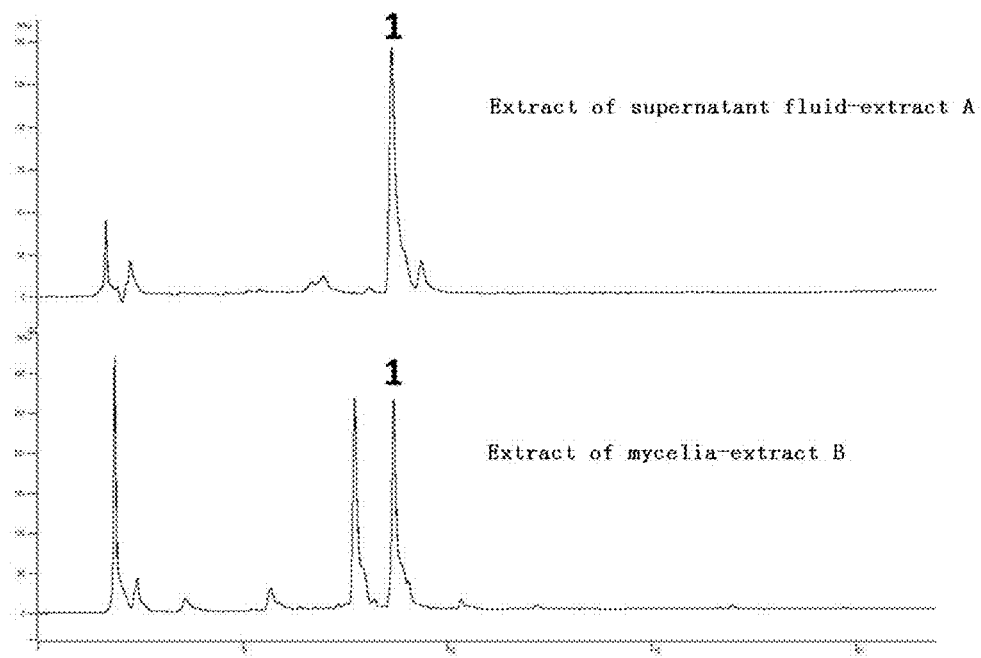
FIG. 3 is a high-performance liquid chromatogram of extract of supernatant fluid (extract A) and extract of mycelia (extract B), wherein 1 is Deoxynyboquinone; the HPLC (high-performance liquid chromatography) conditions are as follows: a chromatographic column is of phenomex 150×4.6 mm (SphereClone SAX), mobile phases comprise a mobile A phase and a mobile B phase, the mobile A phase comprises 10% (volume fraction) of acetonitrile and 0.08% (volume fraction) of trifluoroacetic acid, with water serving as a solvent, and the mobile B phase comprises 90% (volume fraction) of acetonitrile, with water serving as the solvent. The sample injection procedure is as follows: from 0 to 20 min, the ratio of the mobile A phase/the mobile B phase (volume ratio) is 95:5-0:100, from 20 to 21 min, the ratio of the mobile A phase/the mobile B phase (volume ratio) is 0:100, from 21 to 22 min, the ratio of the mobile A phase/the mobile B phase (volume ratio) is 0:100-95:5, and from 22 to 30 min, the ratio of the mobile A phase/the mobile B phase (volume ratio) is 95:5, the detection wavelength is 254 nm and the flow rate is 1 ml/min.

HPLC detection (as shown in FIG. 3) shows that Deoxynyboquinone (No. 1 peak) is contained in each of the extract A and the extract B. The extract A and the extract B are mixed, normal-pressure silica gel column (300-400 meshes) chromatography is performed on a crude extract after mixing, chloroform/methanol is taken as eluent, gradient elution is performed in the volume ratio of 100:0 to 0:100, a fraction Fr.1 (1.2 g) which is obtained by gradient elution when the chloroform/methanol volume ratio is 100:1 is collected, drying is performed by distillation, a Sephadex LH-20 gel column is passed, chloroform/methanol in the volume ratio of 1:1 is taken as a mobile phase for elution, and recrystallization is further performed under the condition that the chloroform/methanol volume ratio is 10:1 to get a compound 1 (150.3 mg).

Figure 4:
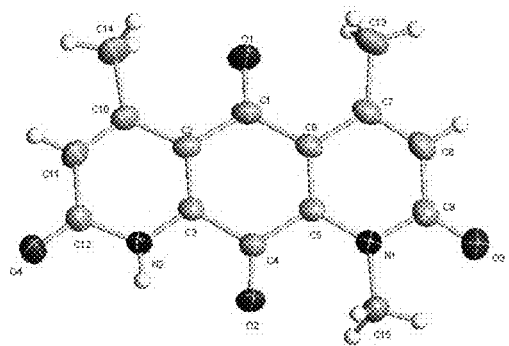
FIG. 4 is an X-diffractogram of compound 1 (Deoxynyboquinone).

Through structural analysis, the identification results of the compound 1 prepared from the fermentation culture of the *Pseudonocardia* sp. SCSIO 01299 disclosed by the invention are as follows:

Compound 1: red needle crystals (methanol), $UV^{(CH3CN:H2O:Trifluoroacetic\ acid)}$: 203.0, 276.3, 353.8, 460.7 nm $^1$H NMR (500 MHz, $CDCl_3$) and $^{13}$C NMR (125 MHz, $CDCl_3$), see Table 1. ESIMS m/z 285.0 [M+H]$^+$, 569.7 [2M+H]$^+$, 283.2 [M−H]$^-$, 567.4 [2M−H]$^-$. From a hydrogen spectrum and a carbon spectrum, we can see that the compound 1 contains 3 methyl groups, namely one single-peak methyl group and two double-peak methyl groups[$δ_H$ 4.01 (s, Me-15), 2.59 (d, J=1.0 Hz, Me-16);, 2.55 (d, J=1.0 Hz, Me-17) $δ_C$ 33.9 (q, Me-15), 23.0 (q, Me-16), 22.1 (q, Me-17)], 2 sp$^2$ hybridized methine groups[$δ_H$ 6.82 (d, J=1.0 Hz, H-3), $δ_C$ 126.8 (d, C-3); $δ_H$ 6.78 (d, J=1.0 Hz, H-7), $δ_C$ 127.1 (d, C-7)] and 10 quaternary carbons, namely 6 sp$^2$ hybridized quaternary carbons and 4 carbonyl carbons. According to an HMBC (heteronuclear multiple bond coherence) correlation spectrum, we can see that H-15 is correlated with C-2/C-11, H-3 is correlated with C-2/C-12/C-16, H-16 is correlated with C-3/C-4/C-12, and a ring A can be obtained; H-7 is correlated with C-8/C-13/C-17, H-17 is correlated with C-6/C-7/C-13, and it is speculated that the compound may contain a ring B; and by combining with the 2 carbonyl carbons ($δ_C$ 182.4, 176.9) in the carbon spectrum and the X-diffractogram (FIG. 4), we can determine that the structure is consistent with that of a known compound deoxynyboquinone [Formula (I)].

Formula (I)

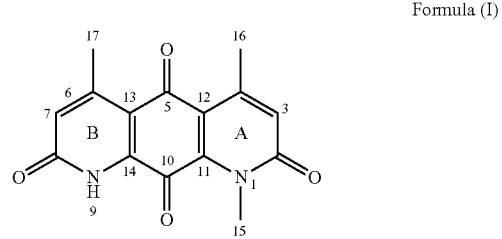

TABLE 1

NMR Data Attribution of Compound 1

| No. | H | C |
|---|---|---|
| 2 |  | 161.4 s |
| 3 | 6.82 (d, 1.0) | 126.8 d |
| 4 |  | 149.0 s |
| 5 |  | 182.4 s* |
| 6 |  | 150.5 s |
| 7 | 6.78 (d, 1.0) | 127.1 d |
| 8 |  | 162.4 s |
| 10 |  | 176.9 s* |
| 11 |  | 114.9 s |
| 12 |  | 141.7 s |

TABLE 1-continued

NMR Data Attribution of Compound 1

| No. | H | C |
|---|---|---|
| 13 |  | 141.4 s |
| 14 |  | 118.2 s |
| 15 | 4.01 s | 33.9 q |
| 16 | 2.59 (d, 1.0) | 23.0 q |
| 17 | 2.55 (d, 1.0) | 22.1 q |

Note:
$^1$H-NMR data is determined at 500 MHz, a coupling constant (Hz) exists in brackets, $^{13}$C-NMR data is determined at 125 MHz, and NMR data is determined in deuterated pyridine.

The invention claimed is:

1. A method for preparing deoxynyboquinone, comprising:
   (a) inoculating an activated culture of *Pseudonocardia* sp. SCSIO 01299 into a seed culture medium, wherein the seed culture medium has a pH of 7.4 and contains per liter thereof: 15 g of starch, 5 g of soybean meal, 15 g of peptone, 15 g of glycerin, 2 g of $CaCO_3$, 30 g of crude sea salt and the balance of water,
   (b) culturing the inoculated seed culture medium at 28° C. and 200 rpm for 48 hours to prepare a seed culture liquid,
   (c) inoculating a volume of the seed culture liquid into a volume of a fermentation culture medium to obtain a 10% (v/v) inoculation amount, wherein the fermentation culture medium has a pH of 7.4 and contains per liter thereof: 15 g of starch, 5 g of soybean meal, 15 g of peptone, 15 g of glycerin, 2 g of $CaCO_3$, 30 g of crude sea salt, dissolved in water,
   (d) shaking a culture of the inoculated fermentation culture medium at 28° C. and 200 rpm for 120 hours, thereby producing a shaken fermentation culture containing deoxynyboquinone, and
   (e) separating said deoxynyboquinone from the fermentation culture grown in step (d).

2. The method for preparing deoxynyboquinone according to claim 1, wherein the separating of step (e) comprises:
   (i) separating a fermentation liquid fraction of the inoculated and/or shaken fermentation culture from a mycelia-containing fraction thereof, comprising:
      extracting the fermentation liquid with butanone, thereby forming a butanone layer, and
      performing distillation and concentration of the butanone layer to obtain a liquid fraction first extract (extract A), then
   (ii) leaching the mycelia with acetone, and recovering the acetone from the mycelia leaching solution wherein the solution remaining after said recovering of acetone comprises an aqueous solution, then
   (iii) extracting the aqueous solution with butanone, thereby forming a second butanone layer, and
   (iv) performing distillation and concentration of the second butanone layer to obtain a second extract (extract B);
   (v) performing silica gel column chromatography on the extract A or the extract B or a crude extract obtained by mixing the extract A and the extract B, comprising:
      performing gradient elution using a gradient of methanol in chloroform as the elution solvent,
      wherein the ratio by volume of the methanol to chloroform changes from 0:100 to 100:0, and
      wherein a first fraction (Fr.1) is eluted at a volume ratio of 1:100, methanol:chloroform, and further passing the collected fraction (Fr.1) through an LH-20 gel column, eluting the gel column with chloroform:methanol in the volume ratio of 1:1 (v/v) as a mobile phase, thereby eluting a fraction containing said deoxynyboquinone, and
   (vi) recrystallizing the deoxynyboquinone-containing eluted fraction, thereby obtaining said deoxynyboquinone.

3. The method for preparing deoxynyboquinone according to claim 2, wherein the recrystallizing is performed in a solvent of chloroform:methanol, at a volume of 10:1 (v/v).

* * * * *

SEQUENCE LISTING

<160> NUMBER OF SEQ ID NOS: 1

<210> SEQ ID NO 1
<211> LENGTH: 1435
<212> TYPE: DNA
<213> ORGANISM: Pseudonocardia species
<220> FEATURE:
<221> NAME/KEY: misc_feature
<223> OTHER INFORMATION: SCSIO 01299 strain

<400> SEQUENCE: 1

```
gcttaccatg cagtcgagcg gtaaggccct tcgggggta cacgagcggc gaacgggtga      60
gtaacacgtg ggtgacctgc cctccactct gggataagcc cgggaaactg ggtctaatac    120
cggataggac ctctcaacgc atgttgggtg gtggaaagtt ttttcggtgg gggatgggcc    180
cgcggcctat cagcttgttg gtggggtgat ggcctaccaa ggcggtgacg ggtagccggc    240
ctgagagggc gaccggccac actgggactg agacacggcc cagactccta cgggaggcag    300
cagtggggaa tattgcgcaa tgggcggaag cctgacgcag cgacgccgcg tggggatga    360 cggccttcgg gttgtaaacc tctttcgcca gggacgaagc ttttgtgacg gtacctggag    420
aagaagcacc ggccaactac gtgccagcag ccgcggtaac acgtagggtg cgagcgttgt    480
ccggaattat tgggcgtaaa gagctcgtag gcggtgtgtc gcgtcggccg tgaaaacttg    540
gggcttaact ctgagcgtgc ggtcgatacg ggcatcactt gagttcggca ggggagactg    600
gaattcctgg tgtagcggtg aaatgcgcag atatcaggag gaacaccggt ggcgaaggcg    660
ggtctctggg ccgatactga cgctgaggag cgaaagcgtg gggagcgaac aggattagat    720
accctggtag tccacgccgt aaacgttggg cgctaggtgt ggggaccatt ccacggtttc    780
tgcgccgcag ctaacgcatt aagcgccccg cctggggagt acggccgcaa ggctaaaact    840
caaaggaatt gacggggggcc cgcacaagcg gcggagcatg tggattaatt cgatgcaacg    900
cgaagaacct tacctgggtt tgacatgcac aggatcgcgg cagagatgtc gtttcccttg    960
tggcctgtgt gcaggtggtg catggctgtc gtcagctcgt gtcgtgagat gttgggttaa   1020
gtcccgcaac gagcgcaacc cttattccat gttgccagca cgtagtggtg gggactcatg   1080
ggagactgcc ggggtcaact cggaggaagg tggggatgac gtcaagtcat catgcccctt   1140
atgtccaggg cttcacacat gctacaatgg ctcatacaga gggctgcgag accgtgaggt   1200
ggagcgaatc ccttaaagtg agtctcagtt cggatcgggg tctgcaactc gacccgtga   1260
```

```
agttggagtc gctagtaatc gcagatcagc aacgctgcgg tgaatacgtt cccgggcctt    1320
gtacacaccg cccgtcacgt cacgaaagtt ggtaacaccc gaagccggcg gcccaaccct    1380
tgtggaggga gtcgtcgaag gtgggactgg cgattgggac gaagtcgtaa caagg         1435
```